US012805861B2

(12) United States Patent
Zimmern

(10) Patent No.: US 12,805,861 B2
(45) Date of Patent: Nov. 24, 2026

(54) SUTURE TENSIONING SYSTEMS, METHODS, AND DEVICES

(71) Applicant: The Board of Regents of the University of Texas System, Austin, TX (US)

(72) Inventor: Philippe E. Zimmern, Dallas, TX (US)

(73) Assignee: THE BOARD OF REGENTS OF THE UNIVERSITY OF TEXAS, Austin, TX (US)

(*) Notice: Subject to any disclaimer, the term of this patent is extended or adjusted under 35 U.S.C. 154(b) by 63 days.

(21) Appl. No.: 18/728,046

(22) PCT Filed: Feb. 2, 2023

(86) PCT No.: PCT/US2023/061867
§ 371 (c)(1),
(2) Date: Jul. 10, 2024

(87) PCT Pub. No.: WO2023/154657
PCT Pub. Date: Aug. 17, 2023

(65) Prior Publication Data

US 2025/0099095 A1 Mar. 27, 2025

Related U.S. Application Data

(60) Provisional application No. 63/307,731, filed on Feb. 8, 2022.

(51) Int. Cl.

| | |
|---|---|
| ***A61B 17/04*** | (2006.01) |
| *A61B 17/00* | (2006.01) |
| *A61F 2/00* | (2006.01) |

(52) U.S. Cl.
CPC ...... *A61B 17/0469* (2013.01); *A61B 17/0485* (2013.01); *A61B 2017/00526* (2013.01); *A61B 2017/0496* (2013.01); *A61F 2/0045* (2013.01)

(58) Field of Classification Search
CPC ...... A61B 2017/0496; A61B 2090/064; A61B 17/0469; A61B 17/0483; A61B 17/8869;
(Continued)

(56) References Cited

U.S. PATENT DOCUMENTS

| | | | | |
|---|---|---|---|---|
| 6,679,889 B1 | 1/2004 | West, Jr. et al. | | |
| 2007/0049952 A1* | 3/2007 | Weiss | A61B 17/0218 606/144 | |

(Continued)

OTHER PUBLICATIONS

Patent Cooperation Treaty, International Search Report and Written Opinion, International Application No. PCT/US23/61867, date of mailing Jul. 21, 2023, 10 pages.

*Primary Examiner* — Katherine M Shi
(74) *Attorney, Agent, or Firm* — Polsinelli PC

(57) ABSTRACT

Suture tensioning systems, methods, and devices include a suture device for extracting a suture thread from a patient and then determining a location to secure the suture knot based on a balanced tension measurement. The suture device has a needle pass mount with needle passes, and a slidable eyelet assembly positioned opposite the needle passes. The eyelet assembly includes gripping portions for moving the eyelet assembly relative to other components of the suture device. Accordingly, eyelets extending from the eyelet assembly move through the needle pass mounts and extend out the needle passes. With the suture thread secured in the extended eyelet, the eyelet assembly is retracted. The suture thread is attached to a tensioning bar and tension meter. The tension meter indicates if the suture tension is within a threshold range and comparable to the opposite side, and a precise tying location for the suture knot is determined.

18 Claims, 5 Drawing Sheets

(58) Field of Classification Search
CPC . A61B 17/04; A61B 17/0482; A61B 17/0485; A61B 17/06004; A61B 17/06109; A61B 17/06066; A61B 2017/00805; A61B 2017/0472; A61B 2090/0807; A61B 90/06; A61F 2/0045
See application file for complete search history.

(56) References Cited

U.S. PATENT DOCUMENTS

| | | | | |
|---|---|---|---|---|
| 2008/0228267 | A1* | 9/2008 | Spence | A61B 17/0487 623/2.36 |
| 2016/0367368 | A1 | 12/2016 | Vidlund et al. | |
| 2018/0008330 | A1* | 1/2018 | Taber | A61B 17/0401 |
| 2018/0103947 | A1* | 4/2018 | Nobles | A61B 17/0483 |
| 2019/0298429 | A1 | 10/2019 | Osti | |
| 2020/0015971 | A1 | 1/2020 | Brauon et al. | |
| 2020/0281584 | A1 | 9/2020 | Nobles et al. | |

* cited by examiner

SUTURE TENSIONING SYSTEMS, METHODS, AND DEVICES

CROSS-REFERENCE TO RELATED APPLICATION

This application claims priority to U.S. Provisional Application No. 63/307,731, filed Feb. 8, 2022 and titled "Suture Tensioning Systems, Methods, and Devices, which is incorporated by reference in its entirety.

BACKGROUND

1. Field

The present disclosure relates generally to systems and methods for securing sutures during a medical procedure. In at least one example, the present disclosure relates to a system configured to tension sutures for a sling procedure.

2. Discussion of Related Art

A sling placement is a procedure to correct stress urinary incontinence in which a strip is placed underneath the urethra to compress the sphincteric mechanism and achieve better continence. The strip is held in place by a string that the surgeon manually secures in place at a suprapubic location using a clamp or needle passer. Once in place, the strip is suspended by the string and acts as a hammock to support the urethra.

However, if the supporting string is tied too tightly, then the result is complete dryness or lifelong retention managed by intermittent catheter drainage (e.g., via intermittent catheterization). If tied too loosely, the procedure fails and incontinence persists. The manual placement of the strings is made even more difficult due to the position of the patient during the procedure—lying flat (supine) on a table and relaxed under anesthesia. The tensioning process is not codified and has inconsistent patient outcomes, resulting in additional complications for the sling procedure, patient suffering, additional hospitalization time, and extra costs.

It is with these observations in mind, among others, that various aspects of the present disclosure were conceived and developed.

BRIEF SUMMARY

The presently disclosed technology addresses the foregoing problems by providing systems, methods and devices to tension a suture during a medical procedure. For instance, a method can comprise: securing the suture to a distal end of tissue internal to a patient; securing one or more threads of the suture to a tensioning device; pulling the one or more threads of the suture, using the tensioning device, to a suture transfer location spaced a distance from the distal end; determining, with the tensioning device, that the one or more threads of the suture have a tension value within a predetermined tension range; securing the one or more threads of the suture at the suture transfer location at least partly in response to the tension value determined by the tensioning device being within the predetermined tension range; and separating the tensioning device from the one or more threads of the suture by severing the one or more threads of the suture at a thread cutting location external to the patient.

In some examples, securing the one or more threads of the suture to the tensioning device includes: inserting a suture pass needle of the tensioning device into an area proximate to the suture internal to the patient; pushing, using a gripping portion of the tensioning device external to the patient, a spring-loaded eyelet through the suture pass needle; and passing the one or more threads of the suture through the spring-loaded eyelet. The spring-loaded eyelet can include a blunt tip. Furthermore, the method can include passing the one or more threads of the suture through a suture pass needle mount; and attaching the one or more threads of the suture to a tensioning bar. In some instances, the medical procedure is a sling procedure and/or a suspension procedure. The distal end of the tissue can be positioned in the vaginal wall below a urethra of the patient, or positioned below a bladder base of the patient. Moreover, the suture transfer location can be a suprapubic location. The one or more threads can be a plurality of threads; and the method can further comprise establishing an even weight distribution for the plurality of threads to create a balanced suspension of the tissue internal to the patient. In some instances, the tensioning device includes: a suture pass needle coupled to a first side of a suture pass needle mount, the one or more threads of the suture passing through an eyelet extending out of the suture pass needle, a gripping portion for moving the eyelet between an extended position and a retracted position, a tensioning bar connected to the suture pass needle mount at a second side opposite the first side via the one or more threads of the suture, and a tension meter coupled to the tensioning bar opposite the suture pass needle mount to measure the tension value of the one or more threads of the suture. Additionally, the tensioning bar can be connected to the suture pass needle mount by the one or more threads of the suture passing through the suture pass needle mount.

In some instances, a tensioning device operable to tension a suture during a medical procedure comprises: a suture pass needle coupled to a first side of a suture pass needle mount; an eyelet disposed in the suture pass needle to receive a thread of the suture, the suture operable to secure to a distal end of tissue internal to a patient; a gripping portion coupled to the eyelet for moving the eyelet relative to the suture pass needle; and a tension meter operable to measure a tension value of the thread when the tensioning device pulls the suture to a suture transfer location spaced a distance from the distal end of the tissue internal to the patient.

Furthermore, the tensioning device can comprise a tensioning bar operable to connect to the tension meter and receive the thread of the suture from a side of the suture pass needle mount opposite the suture pass needle. The tensioning bar can be removably couplable to the suture pass needle mount via the thread of the suture passing through the suture pass needle mount. Furthermore, the eyelet can be a spring-loaded eyelet retracted into the suture pass needle in a resting position and extending out of the suture pass needle in an extended position.

Additionally, in some instances, the suture pass needle is a first suture pass needle, the eyelet is s first eyelet, and the thread is a first thread of the suture, and the tensioning device further includes a second suture pass needle coupled to the first side of the suture pass needle. Moreover, the tensioning device can further comprise: an indicator operable to indicate whether the tension value is within a predetermined tension range.

In some examples, a method of manufacturing a tensioning device operable to tension a suture during a medical procedure comprises: coupling a suture pass needle to a first side of a suture pass needle mount; attaching an eyelet assembly to a second side of the suture pass needle mount opposite the first side, the eyelet assembly including an eyelet operable to receive a thread of the suture and coupled to a gripping portion for retracting the eyelet into the suture pass needle; providing a tensioning bar that is couplable to the suture pass needle mount via the thread of the suture; and providing a tension meter couplable to the tensioning bar, the tension meter operable to measure a tension value of the thread when the tensioning device pulls the suture to a suture transfer location.

In some instances, the suture pass needle is a first suture pass needle, the thread of the suture is a first thread of the suture, the eyelet is a first eyelet, the method further includes coupling a second suture pass needle to the first side of the suture pass needle mount parallel to the first suture pass needle, and the eyelet assembly further includes a second eyelet operable to receive a second thread of the suture and is coupled to the gripping portion for retracting the second eyelet into the second suture pass needle. The eyelet assembly can further include one or more guide rails extending from the second side of the suture pass needle mount such that the gripping portion slides along the one or more guide rails to retract the first eyelet into the first suture pass needle and the second eyelet into the second suture pass needle. Additionally, the eyelet assembly can include a handle extending from the second side of the suture pass needle mount, and the gripping portion can include one or more gripping protrusions extending away from the handle that are slidable relative to the handle. The first suture pass needle and the second suture pass needle can extend with a curve.

The foregoing is intended to be illustrative and is not meant in a limiting sense. Many features of the embodiments may be employed with or without reference to other features of any of the embodiments. Additional aspects, advantages, and/or utilities of the presently disclosed technology will be set forth in part in the description that follows and, in part, will be apparent from the description, or may be learned by practice of the presently disclosed technology.

BRIEF DESCRIPTION OF THE DRAWINGS

The foregoing summary, as well as the following detailed description, will be better understood when read in conjunction with the appended drawings. For the purpose of illustration, there is shown in the drawings certain embodiments of the disclosed subject matter. It should be understood, however, that the disclosed subject matter is not limited to the precise embodiments and features shown. The accompanying drawings, which are incorporated in and constitute a part of this specification, illustrate an implementation of systems and methods consistent with the disclosed subject matter and, together with the description, serves to explain advantages and principles consistent with the disclosed subject matter, in which.

DETAILED DESCRIPTION

Figure 1:
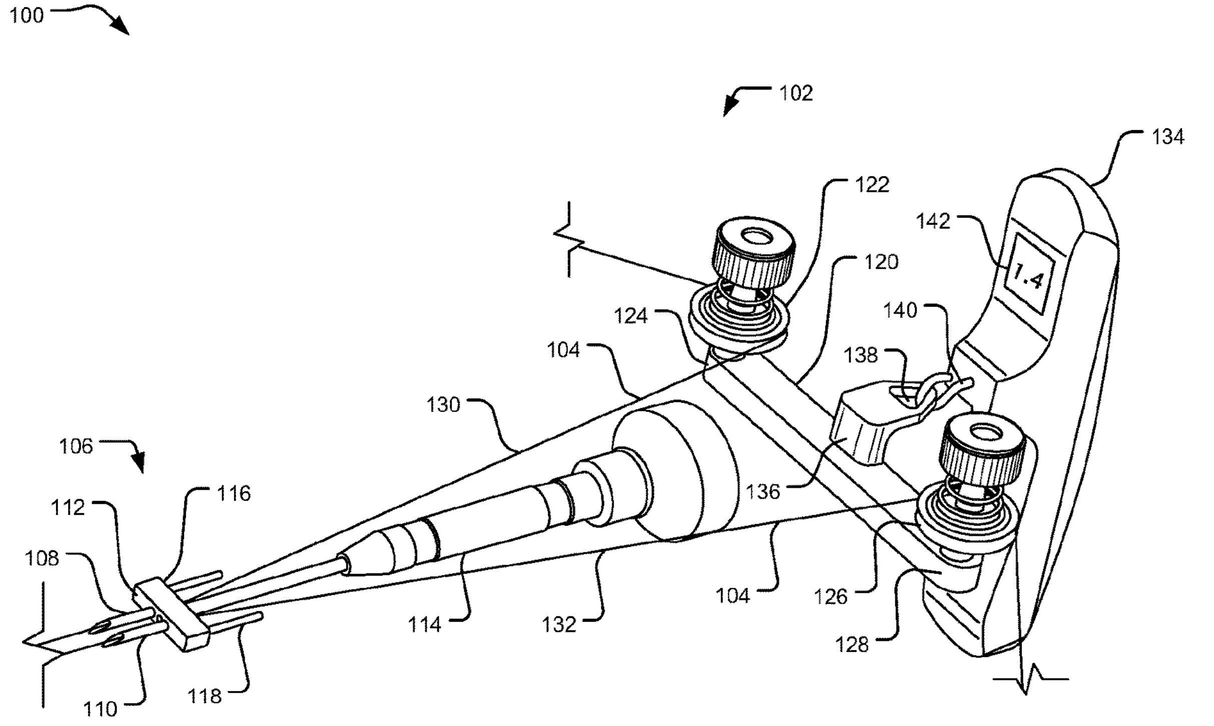
FIG. 1 illustrates an example system for tensioning a suture within a predetermined tension range.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

I. Terminology

The phraseology and terminology employed herein are for the purpose of description and should not be regarded as limiting. For example, the use of a singular term, such as, “a” is not intended as limiting of the number of items. Also, the use of relational terms such as, but not limited to, “top,” “bottom,” “left,” “right,” “upper,” “lower,” “down,” “up,” and “side,” are used in the description for clarity in specific reference to the figures and are not intended to limit the scope of the presently disclosed technology or the appended claims. Further, it should be understood that any one of the features of the presently disclosed technology may be used separately or in combination with other features. Other systems, methods, features, and advantages of the presently disclosed technology will be, or become, apparent to one with skill in the art upon examination of the figures and the detailed description. It is intended that all such additional systems, methods, features, and advantages be included within this description, be within the scope of the presently disclosed technology, and be protected by the accompanying claims.

Further, as the presently disclosed technology is susceptible to embodiments of many different forms, it is intended that the present disclosure be considered as an example of the principles of the presently disclosed technology and not intended to limit the presently disclosed technology to the specific embodiments shown and described. Any one of the features of the presently disclosed technology may be used separately or in combination with any other feature. References to the terms “embodiment,” “embodiments,” and/or the like in the description mean that the feature and/or features being referred to are included in, at least, one aspect of the description. Separate references to the terms “embodiment,” “embodiments,” and/or the like in the description do not necessarily refer to the same embodiment and are also not mutually exclusive unless so stated and/or except as will be readily apparent to those skilled in the art from the description. For example, a feature, structure, process, step, action, or the like described in one embodiment may also be included in other embodiments, but is not necessarily included. Thus, the presently disclosed technology may include a variety of combinations and/or integrations of the embodiments described herein. Additionally, all aspects of the present disclosure, as described herein, are not essential for its practice. Likewise, other systems, methods, features, and advantages of the presently disclosed technology will be, or become, apparent to one with skill in the art upon examination of the figures and the description. It is intended that all such additional systems, methods, features, and advantages be included within this description, be within the scope of the presently disclosed technology, and be encompassed by the claims.

Any term of degree such as, but not limited to, "substantially," as used in the description and the appended claims, should be understood to include an exact, or a similar, but not exact configuration. For example, "a substantially planar surface" means having an exact planar surface or a similar, but not exact planar surface. Similarly, the terms "about" or "approximately," as used in the description and the appended claims, should be understood to include the recited values or a value that is three times greater or one third of the recited values. For example, about 3 mm includes all values from 1 mm to 9 mm, and approximately 50 degrees includes all values from 16.6 degrees to 150 degrees.

The term "coupled" is defined as connected, whether directly or indirectly through intervening components, and is not necessarily limited to physical connections. The connection can be such that the objects are permanently connected or releasably connected. The terms "comprising," "including" and "having" are used interchangeably in this disclosure. The terms "comprising," "including" and "having" mean to include, but not necessarily be limited to the things so described. The term "real-time" or "real time" means substantially instantaneously.

Lastly, the terms "or" and "and/or," as used herein, are to be interpreted as inclusive or meaning any one or any combination. Therefore, "A, B, or C" or "A, B, and/or C" mean any of the following: "A," "B," or "C"; "A and B"; "A and C"; "B and C"; "A, B and C." An exception to this definition will occur only when a combination of elements, functions, steps or acts are in some way inherently mutually exclusive.

II. General Architecture

The systems, methods, and devices disclosed herein include a suture tensioning device that can be used intra-operatively, is easy to operate, reliable in its measurements, and can supplant the manual and non-objective ways of performing the suture tensioning procedure. The suture tensioning device can include an eyelet assembly that improves safety for the device operator by utilizing a blunt eyelet rather than a sharp needle, and also places the sutures on equal and symmetrical tension when being tied suprapubically. By placing the threads extending from the sutures on equal and symmetrical tension, the system standardizes and simplifies suture placement, improving outcomes for continence patients. Improved patient outcomes result in less hospitalization time, ultimately improving hospital efficiency and lowering costs. Moreover, the user-friendly devices disclosed herein are reusable with sterilizable components which are easily adjoined to perform a suture tensioning procedure, and disassembled for sterilization (e.g., in an autoclave), simplifying the suture tensioning procedure for the medical personal, further improving efficiency and lowering costs.

For instance, the suture tensioning device can include a needle pass mount with two needle passes extending from a first side and a handle extending from a second side. The needle passes can be inserted into the patient and a slidable and/or removable eyelet assemble at the second side of the needle pass mount can be used to push eyelets through the needle passes into the patient. The eyelets can be spring-loaded and positioned proximate to the suture threads so the surgeon can place the suture threads into the eyelet inside the patient, and use the eyelet assembly to retract the spring-loaded eyelets out of the patient, pulling the suture threads through the needle pass mount and out the second side. Additionally or alternatively, the spring-loaded eyelets can omit springs and/or be pushed and/or pulled manually. A tensioning bar can receive the suture threads and a tension meter attached to the tensioning bar can measure the tension on the suture threads and present an indication of the measurement. In this arrangement, the suture threads can be further pulled and/or released until the measurement reading reaches a desired value (e.g., is above or below one or more predetermined threshold values). In some examples, the suture tensioning device can be attached to a tripod or other stabilizing apparatus to further stabilize and improve accuracy of the tension measurement. The suture threads can be tied off at a suprapubic location specifically chosen for the precise suture tension that the location provides. Multiple sutures can thus be tied with the same or nearly a same tension value (e.g., within a predetermined error range) at various locations on the patient's body, establishing a secure suspension system with evenly distributed weight to support the internal structure of the patient.

As discussed herein, primary applications of these systems, methods, and devices relate to a sling procedure in the management of stress urinary incontinence in women and/or for the repair for pelvic organ prolapse. The systems, methods, and devices can also be used for any other procedures in need of a reliable and reproducible tension for a thread or suture thread. The systems, methods, and device can be used for other applications in which consistent and reliable tensioning improves patient outcomes including at least orthopedic operations, plastic surgery operations, and the like.

Additional advantages of the systems, methods, and devices discussed herein will become apparent from the detailed description below.

FIG. 1 illustrates an example system 100 for tensioning one or more sutures using a suture tensioning device 102. The suture tensioning device 102 can include multiple components for receiving one or more threads of a suture (e.g., suture thread(s) 104) and detecting and/or presenting a tension corresponding to the suture thread(s) 104. Accordingly, the suture tensioning device 102 can tension the sutures to within a predetermined tension range.

In some instances, the suture tensioning device 102 can include a needle pass mount 106 with a first needle pass 108 and a second needle pass 110 extending from a first or front side 112 of the needle pass mount 106. The first needle pass 108 and/or the second needle pass 110 can be a metallic (e.g., or other rigid material such as plastic, ceramics, etc.) protrusion with an inner opening or channel for guiding an eyelet through the needle pass mount 106 and receiving and guiding the suture thread(s) 104 through the needle pass mount 106, as discussed in greater detail below. The suture tensioning device 102 can also include one or more gripping portions such as a handle 114 coupled to and extending from a second or back side 116 of the needle pass mount 106, which can be an opposite side relative to the front side 112. The gripping portion can include a variety of forms, such as a round or circular profile, a square profile, a textured section to create additional gripping friction, and the like. Moreover, as discussed in more detail regarding FIGS. 3A and 3B, the gripping portion(s) can include one or more side handles or other slidable portions for extending and retracting the eyelets. For instance, an eyelet assembly (e.g., eyelet assembly 302 in FIGS. 3A and 3B) can slidably couple to the back side 116 and/or mate with one or more guidepost(s) 118 extending from the second or back side 116 (e.g., in an opposite direction and/or parallel to the first needle pass 108 and the second needle pass 110) for moving the eyelet(s).

In some examples, the suture tensioning device 102 includes a tensioning bar 120 which can receive and couple to the suture thread(s) 104, securing the suture thread(s) 104 to the suture tensioning device 102. The tensioning bar 120 can include an elongated body with a first thread coupler 122 at a first distal end 124 and a second thread coupler 126 at a second distal end 128. The first thread coupler 122 can receive a first suture thread 130 of the one or more suture thread(s) 104 and the second thread coupler 126 can receive a second suture thread 132 of the one or more suture thread(s) 104. The first thread coupler 122 and the second thread coupler 126 can include one or more of a clamp, a screw-type clamp, a spring-loaded clamp, a groove, an adhesive, a post, and/or the like for securing the suture threads 104. In other words, the first thread coupler 122 and the second thread coupler 126 can be configured to releasably couple the suture thread(s) 104 to the tensioning bar 120.

In some instances, the suture tensioning device 102 includes a tension meter 134 coupled to the tensioning bar 120. For instance, the tensioning bar 120 can include a meter mounting portion 136, which can be located at or near a center line of the tensioning bar 120 between the first distal end 124 and the second distal end 128. The meter mounting portion 136 can link the tensioning bar 120 to the tension meter 134, for instance, with an opening 138 that receives a tension meter coupler 140 of the tension meter 134 (e.g., a hook). In this way, the tension meter 134 can be releasably coupled to the tensioning bar 120. Upon securing the suture thread(s) 104 to the tensioning bar 120, the tension meter 134 can detect a tension of the thread(s) 104 by measuring a force experienced by the tension meter coupler 140 as the suture tensioning device 102 is pulled in a direction away from the sutures and/or the patient. Due to the alignment of the components of the suture tensioning device 102, the tension experienced at the tension meter coupler 140 can correspond to the tension experienced at the suture thread(s) 104. In some instances, the tension experienced at the tension meter coupler 140 is an aggregated tension of a first tension experienced by the first suture thread 130 and a second tension experienced by the second suture thread 132. The tension meter 134 can include a tension indicator 142 for presenting a measured value (e.g., in newtons, pounds, grams, etc.), corresponding to the tension (e.g., force) sensed by the tension meter 134. The tension indicator 142 can be a gauge or analogue gauge that moves a needle to correspond to the tension.

Additionally or alternatively, the tension indicator 142 can include electronic or digital components, such as a digital display to present the measured value, one or more microphones to generate audio indicating the measured value, one or more haptic or tactile devices to indicate the measured value, and the like. In some examples, the tension indicator 142 can indicate whether the measured value is above or below a predetermined threshold value and/or within a predetermined threshold range. For instance, in the gauge may have a marked or highlighted portion showing an acceptable range of values for the needle to fall on, and/or a digital visualization may indicate whether the measured value is in the predetermined range, for instance, by blinking and/or illuminating a particular icon or light-emitting diode (LED) to that effect. An audio cue (e.g., a beep, an audio file with voice instructions, etc.) and/or the haptic feedback (e.g., a vibration or a pulse) may also indicate whether the measured value is within the predetermined threshold range. As such, a tension value of the suture thread(s) 104 can be determined and presented to a user of the suture tensioning device 102 to improve the suture tensioning procedure by increasing consistency and accuracy of the tension being applied to the suture thread(s) 104.

In some examples, the needle pass mount 106 and the gripping portions (e.g., the handle 114) can be a separable component of the suture tensioning device 102 with respect to the tensioning bar 120 and/or the tension meter 134. For instance, the needle pass mount 106 and the gripping portions may be integral and/or mated together to form a first portion of the suture tensioning device 102, and the tensioning bar 120 and the tension meter 134 can be integral and/or mated together to form a second portion of suture tensioning device 102. The first portion and the second portion can be coupled to each other by the suture thread(s) 104 passing through the needle pass mount 106 and extending out the back side 116 to mate with the first thread coupler 122 and/or the second thread coupler 126. Upon completing the suture tensioning procedure, the suture thread(s) 104 can be removed from the suture tensioning device 102, decoupling the first portion from the second portion. However, in other scenarios, the components of the suture tensioning device 102 can be fully integrated, such that the needle pass mount 106, the gripping portion(s), the tensioning bar 120 and/or the tension meter 134 are integrated together to form a single unit, and remain coupled regardless of whether the suture thread(s) 104 are coupling the tensioning bar 120 to the needle pass mount 106.

Figure 2:
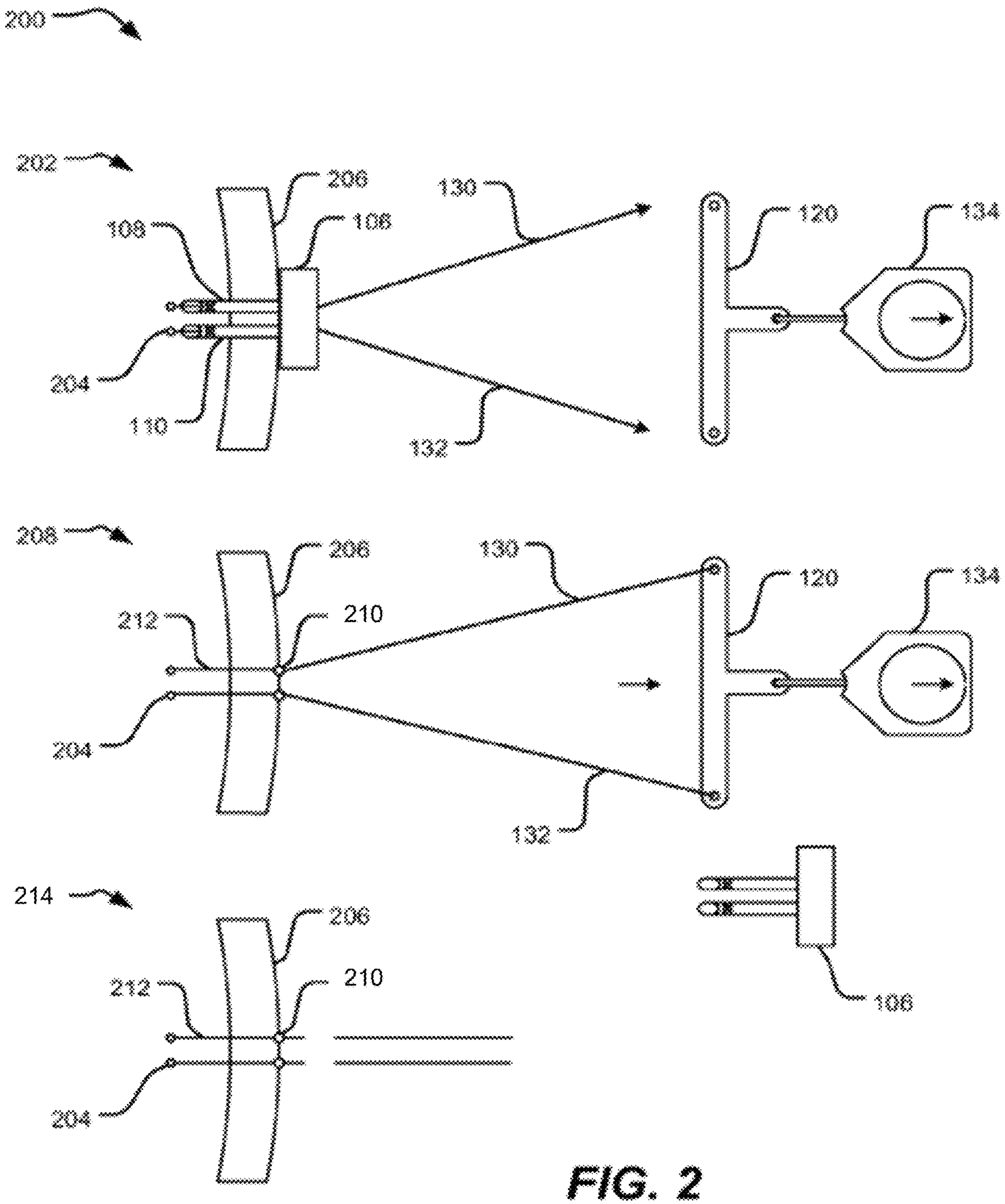
FIG. 2 illustrates an example system for tensioning a suture including an eyelet passing stage and a suture thread positioning stage, which can form at least a portion of the system depicted in FIG. 1.

FIG. 2 illustrates an example system 200 for tensioning one or more sutures using the suture tensioning device 102, which can form at least a portion of the system 100. The system 200 can involve using the suture tensioning device 102 for different stages of the suture tensioning procedure.

In some examples, the system 200 can include an eyelet passing stage 202 in which the suture thread 104 is passed through an eyelet extending out an open end of the first needle pass 108. For instance, a user of the suture tensioning device 102 and/or medical personnel can initiate the suture tensioning procedure by securing a suture 204 to a distal end of tissue internal to the patient, such as a sling or hammock for a sling procedure. The tissue internal to the patient can be a strip of, for instance, synthetic material, biological tissue, human tissue, animal tissue, a xenograft, an autograft, combinations thereof, and the like. Once the suture 204 is secured to the tissue, the first suture thread 130 and/or the second suture thread 132 used to tie the suture 204 can remain extending from the suture 204. The needle passes (e.g., the first needle pass 108 and/or the second needle pass 110) of the suture tensioning device 102 can be inserted into the patient, for instance, by piercing an epidermal surface 206 of the patient to enter the interior portion of the patient. With the needle passes inserted into the patient, the user of the suture tensioning device 102 can guide the first suture thread 130 into a first eyelet extending from the first needle pass 108, and the second suture thread 132 into a second eyelet extending form the second needle pass 110 (e.g., first eyelet 318 and second eyelet 320, as discussed regarding FIGS. 3A and 3B). The first eyelet and the second eyelet can be retracted into the first needle pass 108 and the second needle pass 110, respectively, pulling the first suture thread 130 and the second suture thread 132 through the needle pass mount 106 (e.g., which can be external to the patient and/or abutting the epidermal surface 206) and out the back side 116 of the needle pass mount 106. Then the first suture thread 130 can be secured to the first thread coupler 122 and the second suture thread 132 can be secured to the second thread coupler 126, as discussed above.

In some instances, the suture tensioning procedure can include a suture thread positioning and tying stage 208, which can follow the eyelet passing stage 202. For instance, the suture thread positioning and tying stage 208 can include moving or pulling the suture tensioning device 102 away from the suture 204 and the patient (e.g., the epidermal surface 206), creating the tension on the first suture thread 130 and the second suture thread 132 between the suture 204 and the tensioning bar 120. The tension indicator 142 of the tension meter 134 can indicate that the measured value of the tension is within a predetermined threshold range (e.g., above a first predetermined threshold value, below a second predetermined threshold value, and the like). In response, the first suture thread 130 and the second suture thread 132 can be secured in place at a suture transfer location 210. The predetermined threshold range can be based on a variety of factors and/or can correspond to an age of the patient undergoing the suture tensioning procedure, a body weight of the patient, a severity of bladder leakage of the patient, and combinations thereof. In some instances, the predetermined threshold range and/or predetermined threshold values can include tension values of between 0.1 newton and 10 newtons.

The suture transfer location 210 can be a suprapubic location on the epidermal surface 206 of the patient (e.g., external to the patient). By securing the suture thread(s) 104 at the suture transfer location 210 in response to the tension being within the predetermined range, consistent tensions for internal portions 212 of the suture thread(s) 104 remaining in the patient—connecting the suture 204 inside the patient to the suture transfer location 210—can be established. Consistent tensions for both the first suture thread 130 and the second suture thread 132 of the suture 204, as well as other suture threads 104 of another suture connecting another side of the sling tissue, can be established and maintained. Once the suture thread(s) 104 are secured or tied at the suture transfer location 210 with the predetermined tension, the suture tensioning procedure can include a thread severing stage 214 in which the remaining portions of the suture thread(s) 104 beyond the tie offs at the suture transfer location 210 are cut or severed. This can conclude the suture tensioning procedure.

Figure 3A:
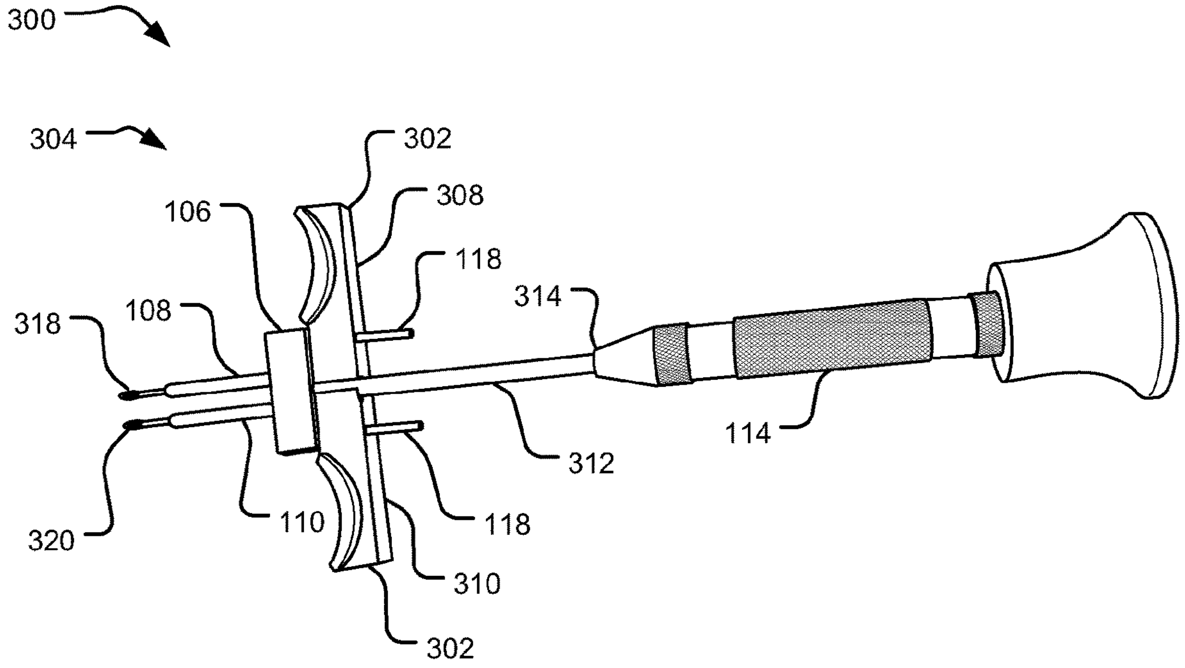
FIG. 3 illustrates an example system for tensioning a suture including an eyelet assembly movable between different positions, which can form at least a portion of the system depicted in FIG. 1.
Figure 3B:
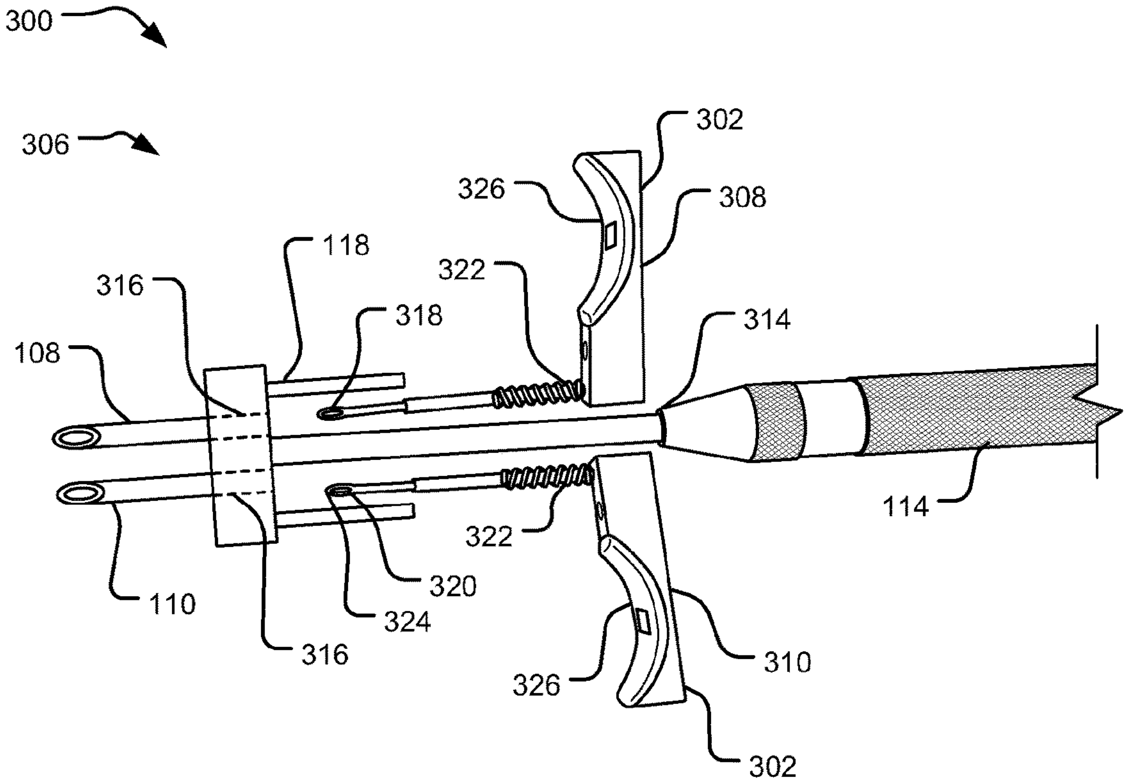

FIGS. 3A and 3B illustrate an example system 300 for tensioning one or more sutures using the suture tensioning device 102, which can form at least a portion of the system 100. The suture tensioning device 102 of system 300 can include an eyelet assembly 302 movable between multiple positions, such as an extended position 304, a retracted position, and/or a separated position 306.

In some examples, the eyelet assembly 302 includes gripping portion protrusions in addition to the handle 114, such as a first side grip 308 and/or a second side grip 310 (e.g., the side grip(s)). The first side grip 308 can extend away from and/or be perpendicular to the handle 114 or an axis defined by the handle 114. Likewise, the second side grip 310 can extend away from and/or be perpendicular to the handle 114 or an axis defined by the handle 114, and in a direction opposite the first side grip 308. The side grip(s) 308 and 310 can be movable (e.g., slidable) relative to the handle 114 and the needle pass mount 106. The needle pass mount 106 can couple to the handle 114 via a handle stem 312 extending from a distal end 314 of the handle 114 to the back side 116 of the needle pass mount 106, and the first side grip 308 and the second side grip 310 can be positioned around the handle stem 312 (e.g., via side grooves in the first side grip 308 and the second side grip 310 shaped to fit around the handle stem 312). Additionally, the first side grip 308 and the second side grip 310 can include post holes for receiving the guidepost(s) 118 extending from the back side 116 of the needle pass mount 106. The needle pass mount 106 can have eyelet channel(s) 316 or openings extending from the back side 116 of the needle pass mount 106 through the body of the needle pass mount 106 and aligned with the first needle pass 108 and/or the second needle pass 110 (e.g., continuous with or forming a line with the openings of the first needle pass 108 and the second needle pass 110).

The channel(s) 316 can be operable to receive a first eyelet 318 extending from the first side grip 308 and a second eyelet 320 extending from the second side grip 310. The first eyelet 318 and the second eyelet 320 can be spring-loaded eyelets with springs 322 positioned around bases of the first eyelet 318 and the second eyelet 320. As such, when the suture tensioning device 102 is in the extended position 304, the first eyelet 318 and the second eyelet 320 can be pushed out the ends of the first needle pass 108 and the second needle pass 110 with the spring 322 compressed. In the retracted position, the first eyelet 318 and the second eyelet 320 can be retracted into at least the first needle pass 108 and the second needle pass 110 with the springs 322 less compressed or at least partly relaxed relative to the extended position 304. In the separated position 306, the first side grip 308 and the second side grip 310 can be separated and/or removed from the needle pass mount 106 with the springs 322 fully relaxed and/or in a resting state. The suture tensioning device 102 can be moved to the separated position 306 at the eyelet passing stage 202 to pull the suture thread(s) 104 through the needle pass mount 106 so they can be tied to the tensioning bar 120. Furthermore, the first eyelet 318 and the second eyelet 320 can have blunt tips 324 (e.g., rounded tips). Accordingly, during the suture tensioning procedure, safety can be improved by using the blunt tips 324 of the first eyelet 318 and the second eyelet 320 to receive the suture thread(s) 104, rather than a sharp needle which can pose a safety concern to the medical personnel attempting to thread the sharp needle from the internal area of the patient without poking themselves.

In some examples, the first side grip 308 and/or the second side grip 310 can include finger indentations 326 with rounded contours designed to keep the fingers of the user in place. In some instances, additional guiderails can extend from the back side 116 the length of the handle (e.g., an entire length of the handle) for sliding the first eyelet 318 and the second eyelet 320 between the different positions. In these scenarios, the extended guide rails can hold the gripping portions at a constant distance from the handle as the gripping portions are used to move the eyelets 318 and 320 between the different positions. Furthermore, in some instances, the needle passes 108 and 110 can include a curved or bent shape as they extend away from the front side 112 of the needle pass mount 106.

Figure 4:
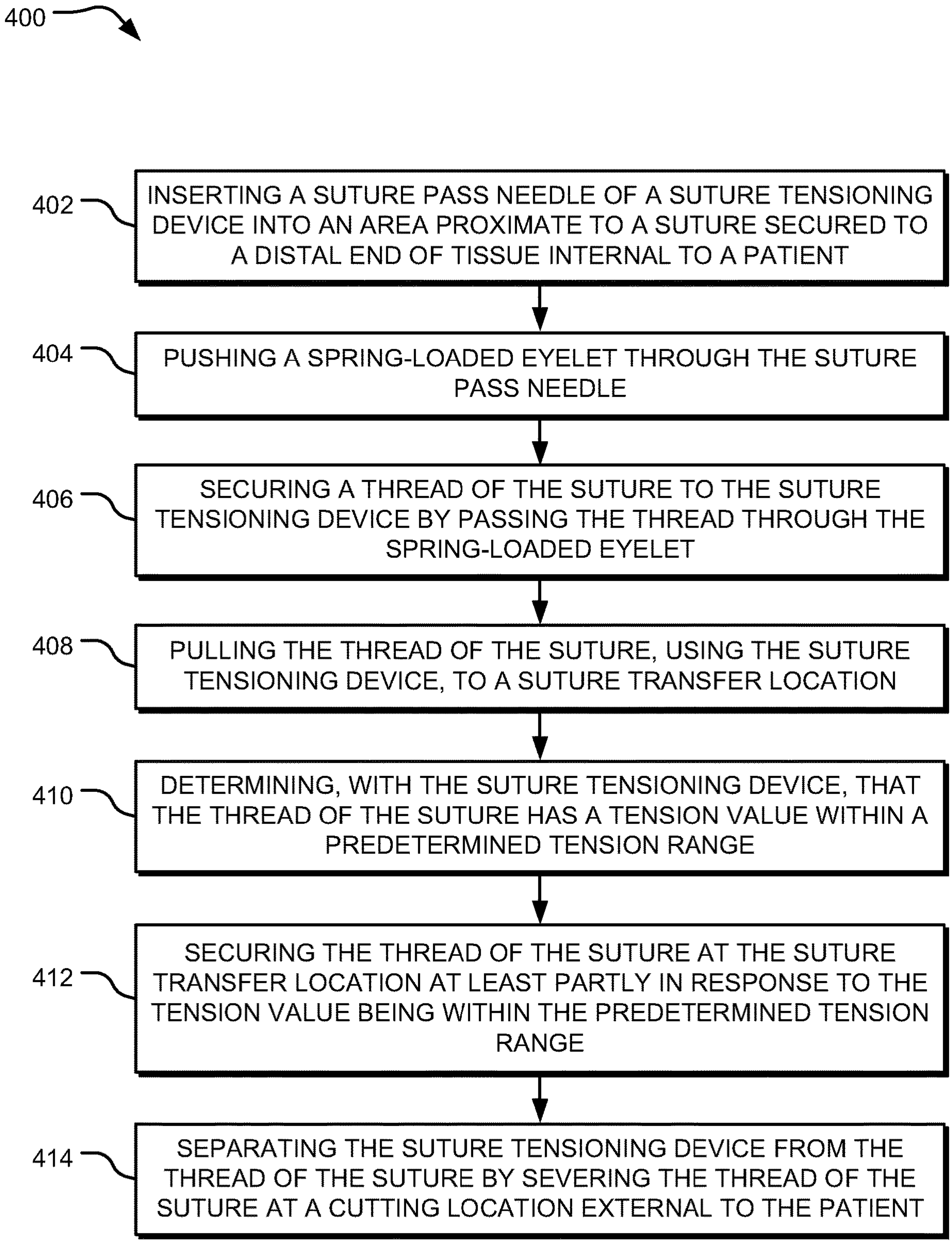
FIG. 4 illustrates an example method for tensioning a suture, which can be performed by the system depicted in FIG. 1.

FIG. 4 illustrates an example method 400 for tensioning a suture during a medical procedure using a suture tensioning device, which can be performed by any of the systems 100-300 disclosed herein.

At operation 402, the method 400 inserts a suture pass needle of a suture tensioning device into an area proximate to a suture secured to a distal end of tissue internal to a patient. At operation 404, the method 400 pushes a spring-loaded eyelet through the suture pass needle. At operation 406, the method 400 secures a thread of the suture to the suture tensioning device by passing the thread through the spring-loaded eyelet. At operation 408, the method 400 pulls the thread of the suture, using the suture tensioning device, to a suture transfer location. At operation 410, the method 400 determines, with the suture tensioning device, that the thread of the suture has a tension value within a predetermined tension range. At operation 412, the method 400 secures the thread of the suture at the suture transfer location at least partly in response to the tension value being within the predetermined tension range. At operation 414, the method 400 separates the suture tensioning device from the thread of the suture by severing the thread of the suture at a cutting location external to the patient.

Figure 5:
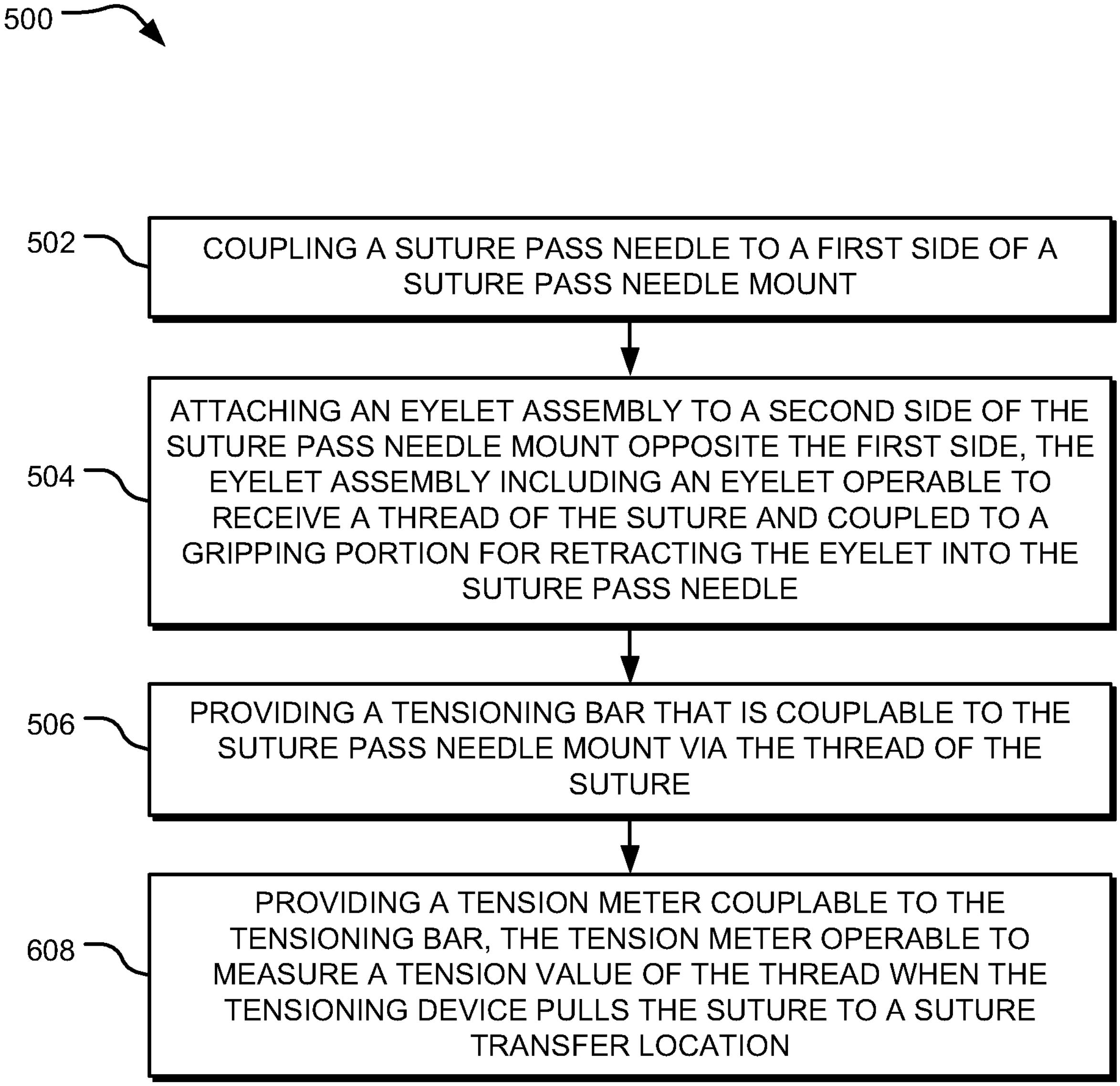
FIG. 5 illustrates an example method for manufacturing a suture tensioning device, which can form at least a portion of the system depicted in FIG. 1.

FIG. 5 illustrates an example method 500 for manufacturing a suture tensioning device, which can form at least a part of any of the systems 100-300 discussed herein.

At operation 502, the method 500 couples a suture pass needle to a first side of a suture pass needle mount. At operation 504, the method 500 attaches an eyelet assembly to a second side of the suture pass needle mount opposite the first side, the eyelet assembly including an eyelet operable to receive a thread of the suture and coupled to a gripping portion for retracting the eyelet into the suture pass needle. At operation 506, the method 500 provides a tensioning bar that is couplable to the suture pass needle mount via the thread of the suture. At operation 508, the method 500 provides a tension meter couplable to the tensioning bar, the tension meter operable to measure a tension value of the thread when the tensioning device pulls the suture to a suture transfer location.

It is to be understood that the specific order or hierarchy of operations in the methods depicted in FIGS. 4 and 5 and throughout this disclosure are instances of example approaches and can be rearranged while remaining within the disclosed subject matter. For instance, any of the operations depicted in FIGS. 4 and 5 and throughout this disclosure may be omitted, repeated, performed in parallel, performed in a different order, and/or combined with any other of the operations depicted in FIG. 4 or 5 or throughout this disclosure.

While the present disclosure has been described with reference to various implementations, it will be understood that these implementations are illustrative and that the scope of the present disclosure is not limited to them. Many variations, modifications, additions, and improvements are possible. More generally, implementations in accordance with the present disclosure have been described in the context of particular implementations. Functionality may be separated or combined differently in various implementations of the disclosure or described with different terminology. These and other variations, modifications, additions, and improvements may fall within the scope of the disclosure as defined in the claims that follow.

What is claimed is:

1. A tensioning device operable to tension a suture during a medical procedure, the tensioning device comprising:

a suture pass needle coupled to a first side of a suture pass needle mount;

an eyelet disposed in the suture pass needle to receive a thread of the suture, the suture operable to secure to a distal end of tissue internal to a patient;

a gripping portion coupled to the eyelet for moving the eyelet relative to the suture pass needle;

a tension meter operable to measure a tension value of the thread when the tensioning device pulls the suture to a suture transfer location spaced a distance from the distal end of the tissue internal to the patient; and a tensioning bar operable to connect to the tension meter, wherein the tensioning bar includes a thread coupler configured to releasably secure the thread of the suture to the tensioning bar.

2. The tensioning device of claim 1, wherein:

the tensioning bar is operable to receive the thread of the suture from a side of the suture pass needle mount opposite the suture pass needle.

3. The tensioning device of claim 1, wherein, the tensioning bar is removably couplable to the suture pass needle mount via the thread of the suture passing through the suture pass needle mount.

4. The tensioning device of claim 1, wherein, the thread coupler includes a screw-type clamp for receiving the thread of the suture.

5. The tensioning device of claim 1, wherein, the suture pass needle is a first suture pass needle, the eyelet is a first eyelet, and the thread is a first thread of the suture, and the tensioning device further includes a second suture pass needle coupled to the first side of the suture pass needle mount.

6. The tensioning device of claim 5, further comprising:

an indicator operable to indicate whether the tension value is within a predetermined tension range.

7. A method of manufacturing a tensioning device operable to tension a suture during a medical procedure, the method comprising:

coupling a suture pass needle to a first side of a suture pass needle mount;

attaching an eyelet assembly to a second side of the suture pass needle mount opposite the first side, the eyelet assembly including an eyelet operable to receive a thread of the suture and coupled to a gripping portion for retracting the eyelet into the suture pass needle;

providing a tensioning bar that is couplable to the suture pass needle mount via the thread of the suture; and providing a tension meter couplable to the tensioning bar, the tension meter operable to measure a tension value of the thread when the tensioning device pulls the suture to a suture transfer location, wherein the tensioning bar includes a screw-type clamp for receiving the thread of the suture.

8. The method of claim 7, wherein, the suture pass needle is a first suture pass needle, the thread of the suture is a first thread of the suture, the eyelet is a first eyelet, the method further includes coupling a second suture pass needle to the first side of the suture pass needle mount parallel to the first suture pass needle, and the eyelet assembly further includes a second eyelet operable to receive a second thread of the suture and is coupled to the gripping portion for retracting the second eyelet into the second suture pass needle.

9. The method of claim 8, wherein, the eyelet assembly further includes one or more guide rails extending from the second side of the suture pass needle mount such that the gripping portion slides along the one or more guide rails to retract the first eyelet into the first suture pass needle and the second eyelet into the second suture pass needle.

10. The method of claim 9, wherein, the eyelet assembly further includes a handle extending from the second side of the suture pass needle mount, and the gripping portion includes one or more gripping protrusions extending away from the handle that are slidable relative to the handle.

11. The method of claim 9, wherein, the first suture pass needle and the second suture pass needle extend with a curve.

12. A tensioning device operable to tension a suture during a medical procedure, the tensioning device comprising:

a suture pass needle coupled to a first side of a suture pass needle mount;

an eyelet disposed in the suture pass needle to receive a thread of the suture, the suture operable to secure to a distal end of tissue internal to a patient;

a gripping portion coupled to the eyelet for moving the eyelet relative to the suture pass needle;

a tension meter operable to measure a tension value of the thread when the tensioning device pulls the suture to a suture transfer location spaced a distance from the distal end of the tissue internal to the patient; and a tensioning bar operable to connect to the tension meter, wherein the tensioning bar includes a screw-type clamp for receiving the thread of the suture.

13. The tensioning device of claim 12, wherein:

the suture pass needle is a first suture pass needle;

the thread of the suture is a first thread of the suture; and the eyelet is a first eyelet.

14. The tensioning device of claim 13, further including:

a second suture pass needle coupleable to the first side of the suture pass needle mount parallel to the first suture pass needle; and an eyelet assembly including a second eyelet operable to receive a second thread of the suture and is coupleable to the gripping portion for retracting the second eyelet into the second suture pass needle.

15. The tensioning device of claim 14, wherein:

the eyelet assembly further includes one or more guide rails extending from a second side of the suture pass needle mount such that the gripping portion slides along the one or more guide rails to retract the first eyelet into the first suture pass needle and the second eyelet into the second suture pass needle.

16. The tensioning device of claim 14, wherein:

the first suture pass needle and the second suture pass needle extend with a curve.

17. The tensioning device of claim 14, wherein:

the eyelet assembly further includes a handle extending from the second side of the suture pass needle mount, and the gripping portion includes one or more gripping protrusions extending away from the handle that are slidable relative to the handle.

18. The tensioning device of claim 12, wherein: the tensioning bar is removably couplable to the suture pass needle mount via the thread of the suture passing through the suture pass needle mount.

* * * * *